(12) United States Patent
Ryan et al.

(10) Patent No.: US 7,699,168 B2
(45) Date of Patent: Apr. 20, 2010

(54) HEART VALVE STORAGE AND SHIPPING RETAINER

(75) Inventors: Timothy R. Ryan, Shorewood, MN (US); Cathy A. Bergin, Hugo, MN (US)

(73) Assignee: Medtronic, Inc., Minneapolis, MN (US)

( * ) Notice: Subject to any disclaimer, the term of this patent is extended or adjusted under 35 U.S.C. 154(b) by 1207 days.

(21) Appl. No.: 11/254,510

(22) Filed: Oct. 20, 2005

(65) Prior Publication Data

US 2006/0113207 A1 Jun. 1, 2006

Related U.S. Application Data

(60) Provisional application No. 60/623,484, filed on Oct. 29, 2004.

(51) Int. Cl.
 *A61B 19/02* (2006.01)
 *A61F 2/24* (2006.01)
(52) U.S. Cl. .................................. 206/438; 623/2.1
(58) Field of Classification Search ............... 206/438, 206/583, 569–572; 623/2.1
 See application file for complete search history.

(56) References Cited

U.S. PATENT DOCUMENTS

| | | | |
|---|---|---|---|
| 4,211,325 A * | 7/1980 | Wright | 206/438 |
| 4,750,619 A | 6/1988 | Cohen et al. | |
| 5,720,391 A | 2/1998 | Dohm et al. | |
| 5,823,342 A | 10/1998 | Caudillo et al. | |
| 5,960,956 A | 10/1999 | Langanki et al. | |
| 6,199,696 B1 * | 3/2001 | Lytle et al. | 206/438 |
| 6,416,547 B1 * | 7/2002 | Erickson et al. | 623/2.11 |
| 6,572,819 B1 * | 6/2003 | Wu et al. | 422/28 |
| 6,702,255 B2 | 3/2004 | Dehdashtian | |
| 6,723,122 B2 | 4/2004 | Yang et al. | |
| 6,908,113 B2 * | 6/2005 | Chaduc et al. | 283/81 |
| 6,916,547 B2 | 7/2005 | Tian et al. | |
| 2002/0161431 A1 * | 10/2002 | Stobie et al. | 623/2.11 |
| 2003/0070944 A1 * | 4/2003 | Nigam | 206/210 |

* cited by examiner

*Primary Examiner*—J. Gregory Pickett
(74) *Attorney, Agent, or Firm*—Mike Jaro; Jeffrey J. Hohenshell

(57) ABSTRACT

This invention relates to a system and apparatus for retaining a prosthetic valve in a valve pocket suspended in a sealed container to protect from damage and contamination during shipment, handling and storage. The apparatus is an easy to open container having remote fill ports for adding a sterile liquid after enclosing the valve inside. A tamper evident seal is provided having a novel configuration to detect prior opening of the container. The apparatus includes an assembly having a shelf that is provided in a variety of configurations. The shelf has a mitral valve configuration and an aortic valve configuration. The shelf is selected based on the valve configurations and size. The system is easily assembled having a single variable component to adapt to a particular prosthetic valve to be stored. The present invention provides an apparatus for eliminating the need for direct attachment of the valve serial tag to the valve.

26 Claims, 8 Drawing Sheets

HEART VALVE STORAGE AND SHIPPING RETAINER

CROSS-REFERENCE TO RELATED APPLICATION

This application claims the benefit of U.S. provisional application No. 60/623,484, filed Oct. 29, 2004, the entire contents of which are herein incorporated by reference.

FIELD OF THE INVENTION

The present invention relates to a system and apparatus for packaging replacement heart valves and the like for storing and shipping after manufacturing. More particularly, the present invention relates to a heart valve retainer for holding a replacement heart valve in a controlled and sterile condition. The present invention also relates to an apparatus from which the surgical personnel can remove the prosthetic heart valve quickly and effectively for use in a patient during heart valve surgery.

BACKGROUND

Heart valves and more specifically prosthetic aortic and mitral valves are manufactured and prepared for insertion into patients during a surgical procedure. The valves must be sterilized after manufacture and stored in a container for shipment to a hospital or surgery center. The valve is then removed from the package, rinsed and prepared for placement in a patient during surgery.

The container preserves the sterile condition of the valve, protects the valve from damage and minimizes the effort needed by the surgical team to prepare and insert the valve. Sterilization is critical and challenging in working with prosthetic devices. The devices are made in a non-sterile environment and sterilized before packaging and shipping. The valve is usually stored in a sterile solution such as a 0.2% Glutaraldehyde solution after sterilization. Glass jars are commonly used because glass resists reacting with the solution, is inexpensive and can withstand sterilization. A retainer holds the valve in a fixed position inside the container to keep it submerged in the solution.

Prior art designs to store and ship prosthetic heart valves include U.S. Pat. No. 4,750,619 to Cohen assigned to Osteonics Corp entitled "PACKAGE WITH TRAY FOR SECURING AND PRESENTING A STERILE PROSTHETIC IMPLANT ELEMENT". In the '619 patent, a package for holding the prosthetic heart valve has a tray which is stored in a hinged receptacle which is sealed to protect against contamination. In all, three containers are used including the sealing cover. In the Dohm U.S. Pat. No. 5,720,391, entitled "PACKAGING HOLDER FOR HEART VALVE PROSTHESIS", the prosthetic is mounted on a holder having a post. The holder is suspended in a plurality of trays each having a lid. The trays are heat sealed to protect the valve. In U.S. Pat. No. 5,823,342 to Caudillo for "PACKAGING FOR MITRAL OR AORTIC HEART VLAVE DEVICE" an outer shell is screwed together to form a housing over a container having an interchangeable holder for an aortic or mitral valve. U.S. Pat. No. 5,960,956, entitled, "STORAGE CONTAINER", describes a container for holding a prosthetic device in a high humidity environment of sterile liquid but not submersing the device.

Manufacturers are making a variety of valve designs and sizes. This variety of size and configuration demands a flexible packaging system to reduce inventory of valve containers and retainers. Accordingly, there is a need for a system or apparatus for packaging prosthetic heart valves that can be configured to different valve designs, valve sizes, and styles with minimal changes. There is also a need for a storage system that is easy to open.

SUMMARY

This invention relates to a novel valve retainer system and apparatus that is flexible in adapting to different valve configurations and sizes. The present invention provides an apparatus for securing a prosthetic valve in a fixed position by suspending a valve pocket in a jar filled with a sterile liquid. The present invention relates to a valve retainer having a body, a shelf and a cap. The body is a generally cylindrical structure with a first end in the jar and a second end adjacent the lid and a ledge supported between the first end and the second end. A shelf is selected having a valve pocket designed for a particular valve size and configuration. The shelf is attached to the body. The valve is placed in the valve pocket in the shelf. The valve and leaflets are protected against damage by being contained in the valve pocket. The cap is inserted into the second end of the body to engage and hold the valve securely in the pocket.

In one embodiment, the present invention comprises an apparatus that facilitates removing the valve from the package and draining away the sterile solution without touching the valve.

Preferably, the present invention comprises a container that is easy to open.

In a preferred embodiment, the invention comprises an apparatus for minimizing inventory required to package prosthetic valves for shipment, sterilization and storage by a configurable storage system.

In another aspect, the present invention provides a packaging system for prosthetic valves that is easy to assemble.

In another aspect, the present invention comprises an apparatus that minimizes exposure to non-sterile surfaces during removal to help maintain the sterile condition of the prosthetic device.

In another embodiment, the present invention is a retainer for holding a sterilized prosthetic valve that is stored in a sealed container and is conveniently removed to hold the valve for rinsing.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The FIGS are not necessarily to scale.

DETAILED DESCRIPTION

The present invention provides a solution to packaging a prosthetic device in a sterile condition for shipment and storage prior to application to a patient.

Figure 1:
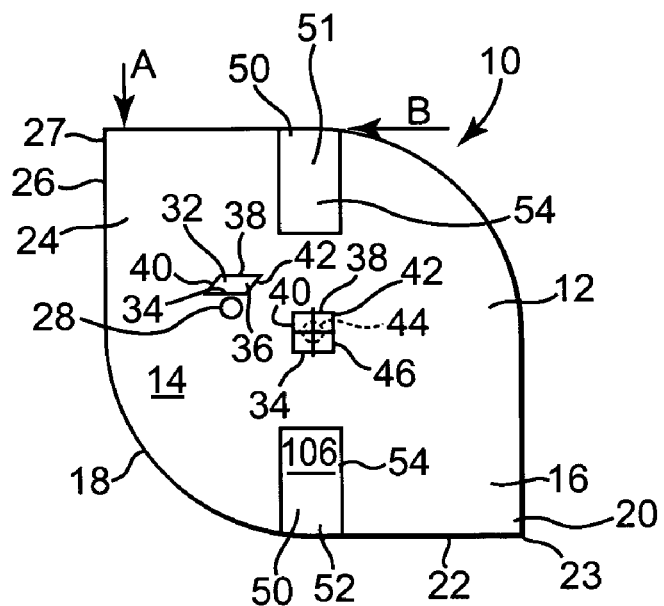
FIG. 1 is a top view of a closed article according to one aspect of the present invention.

FIG. 1 shows a top view of the present invention. The present apparatus 10 is a system for suspending a prosthetic valve in a sterile solution in a container to protect the valve from damage and contamination during shipment handling and storage. The container is shown as jar 56 (FIG. 2) with a removable lid 12 sealingly attached. The lid 12 has a top side 14 and a grip surface 18. A torque enhancing shape 16 is preferably formed in the lid 12. The torque enhancing shape 16 has a first projection 20 on the grip surface 18 defining a first flat 22 and a first point 23. A second projection 24 is disposed on the grip surface 18 at an angular separation from the first projection 20. The second projection 24 has a second flat 26 and a second point 27. In the embodiment shown in FIG. 1, the flats 22, 26 are orientated at a tangent to the circular grip surface 18. The first projection 20 and the second projection 24 enhance the application of torque, by a surgery worker (not shown), to turn and open the lid 12. When the lid 12 is wet, an opening force at arrow A is easier to apply than the same force applied at Arrow B.

Figure 3:
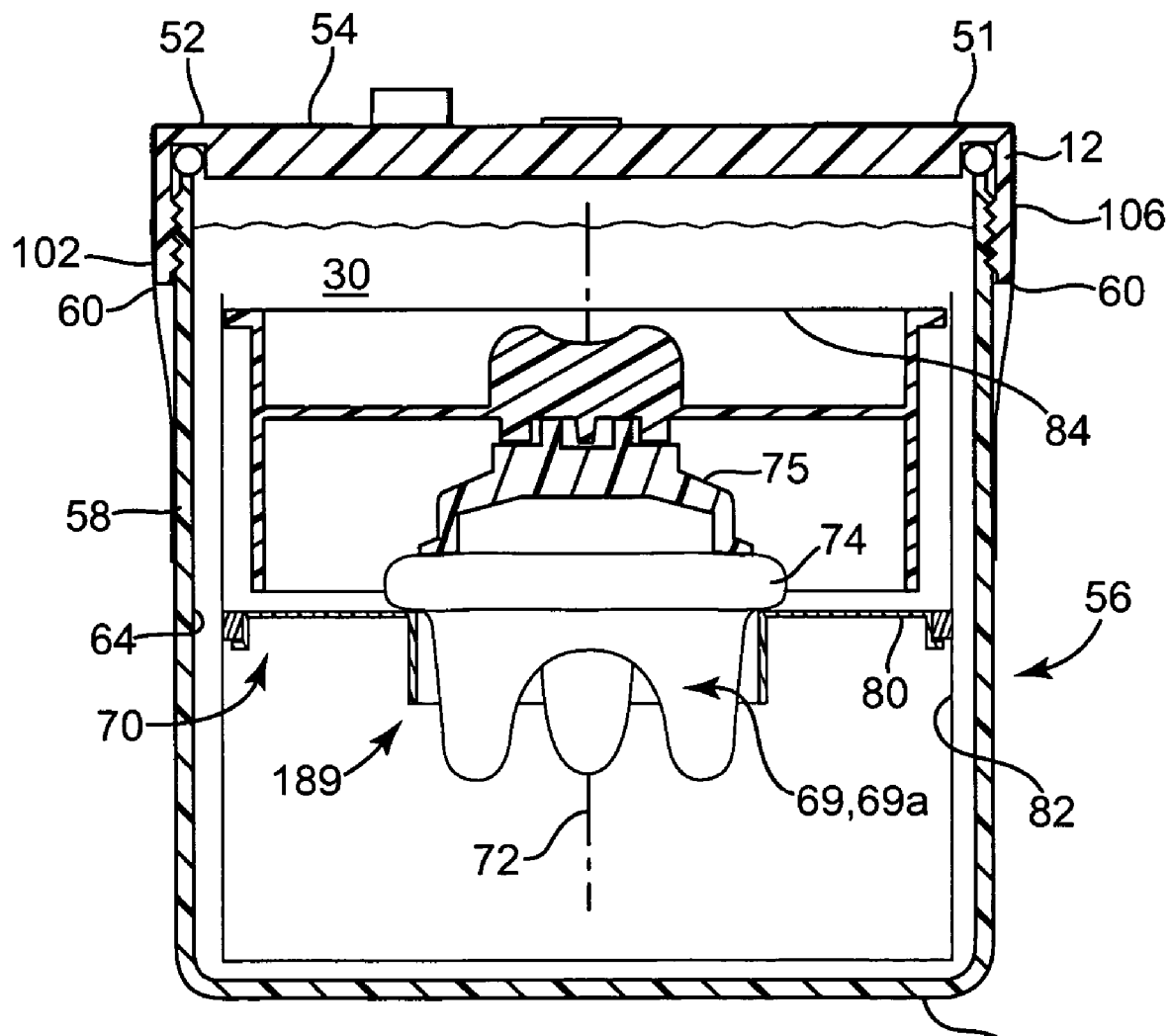
FIG. 3 is side section view taken at approximately 3-3 of FIG. 2.

A first fill hole 28 is formed in the lid 12 to provide access through the top 14 into the storage chamber 30 (FIG. 3). A fold over first tab 32 is formed on the top 14 adjacent the first fill hole 28. The first tab 32 has a bottom surface 36 and a perimeter comprising hinge side 34 on the lid 12, a leading edge 38 and two side edges 40, 42. The hinge side 34 is on the lid 12 adjacent the first fill hole 28. A second fill hole 44 on the top 14 is shown closed by a second tab 46 sealingly connected to the top 14. The second tab 46 is attached by welding the perimeter of the second tab 46 to the top 14 to close the second hole 44. The second tab 46 is similar to the first tab 32. The second tab 46 has a hinge side 34 on the top 14, a top side 48, a leading edge 38 and two side edges 40, 42. The second tab 46 is folded over to cover the second fill hole 44 and sealingly attached to the top 14. The tabs 32, 46 may also be attached to the top 14 by inserting a seal plug, welding or epoxy or the like. The lid 12 may be made of plastic or metal.

Figure 2:
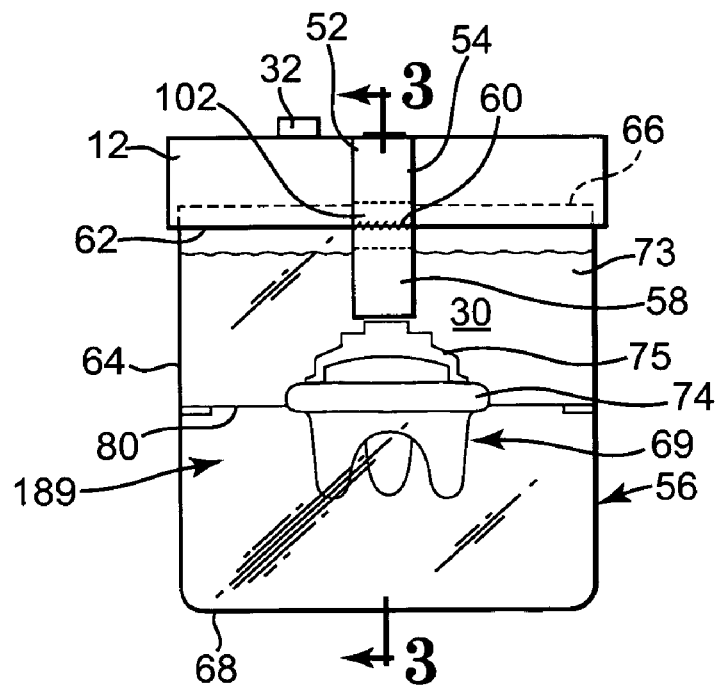
FIG. 2 is a side elevation of FIG. 1.

Referring to FIGS. 1 and 2, a tamper evident seal 50 on the lid 12 comprises a first perforated strip 51 and a second perforated strip 52. The perforated strips 51, 52 are adhesively attached to the lid 12 on the lid end 54 and the jar 56 on the jar end 58 (FIG. 2). A perforation 60 on each strip 51, 52 is aligned at a bottom edge 62 of the lid 12.

The jar 56 has a sidewall 64, an open top 66 and a closed bottom 68 forming an open cylinder shaped storage chamber 30 sealed with the lid 12. The lid 12 is removably attached to the open top 66. The storage chamber 30 has an axis 72 (FIG. 3). A retainer 70 (FIG. 3) is positioned in the jar 56. The retainer 70 (FIG. 3) has a valve pocket 189 suspended between the top 66, the bottom 68 and in spaced relation to the sidewall 64 of the jar 56. The retainer 70 (FIG. 3) prevents damage and contamination to the valve 69 from moving around and bumping against the jar 56. The retainer 70 (FIG. 3) holds the valve 69 submerged in a sterile solution 73 in the jar 56. The valve 69 has a sewing ring 74 attached thereto. A valve holder 75 is removably associated with the sewing ring 74.

Figure 4:
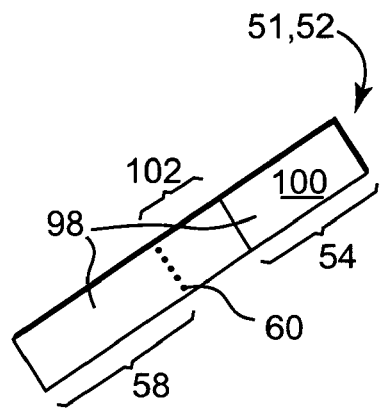
FIG. 4 is a perspective view showing a tamper resistant tag.

Referring to FIGS. 3 and 4, the retainer 70 has a body 82, a shelf 80 and a cap 84. The retainer 70 is a support structure surrounding the storage chamber 30. The retainer 70 extends from the bottom 68 to the top 66 of the jar 56. The shelf 80 on the retainer 70 is mounted in the storage chamber 30 in a position between the top 66 and the bottom 68 of the jar 56. The cap 84 is attached to the body adjacent the shelf 80. The valve is held in a fixed position between the shelf 80 and the cap 84. The retainer 70 is in the jar 56 to support the valve pocket 189 in a position spaced from the sidewall 64 and between the top 66 and bottom 68 of the jar 56 during shipment, handling and storage. The valve 69 sits in the valve pocket 189 with the sewing ring 74 on the shelf 80.

The first and second perforated strips 51, 52 have the perforation 60 aligned with the bottom edge 62 of the lid 12. Referring to FIGS. 3 and 4, an adhesive 98 is placed on the inside 100 of the lid end 54 to thereby attach the lid end 54 of each perforated strip 51, 52 to the lid 12. The perforated strips 51, 52 further comprise a jar end 58 having adhesive 98 on the inside 100 to adhere the jar end 58 to the jar 56. A flag section 102 between the lid end 54 and the perforations 60 is masked during manufacture to prevent adhesive 98 from covering the flag section 102 of the perforations 60. Each perforated strip 51, 52 has an outside 106 for printing information about the seal or the contents of the jar. The perforated strips 51, 52 are made from a flexible paper or plastic material having a coloring to contrast with the lid 12 and the jar 56. One preferred embodiment is a panatone yellow strip. Product labels on the lid 12 and jar 56 may be placed over the ends 54, 58.

Figure 5:
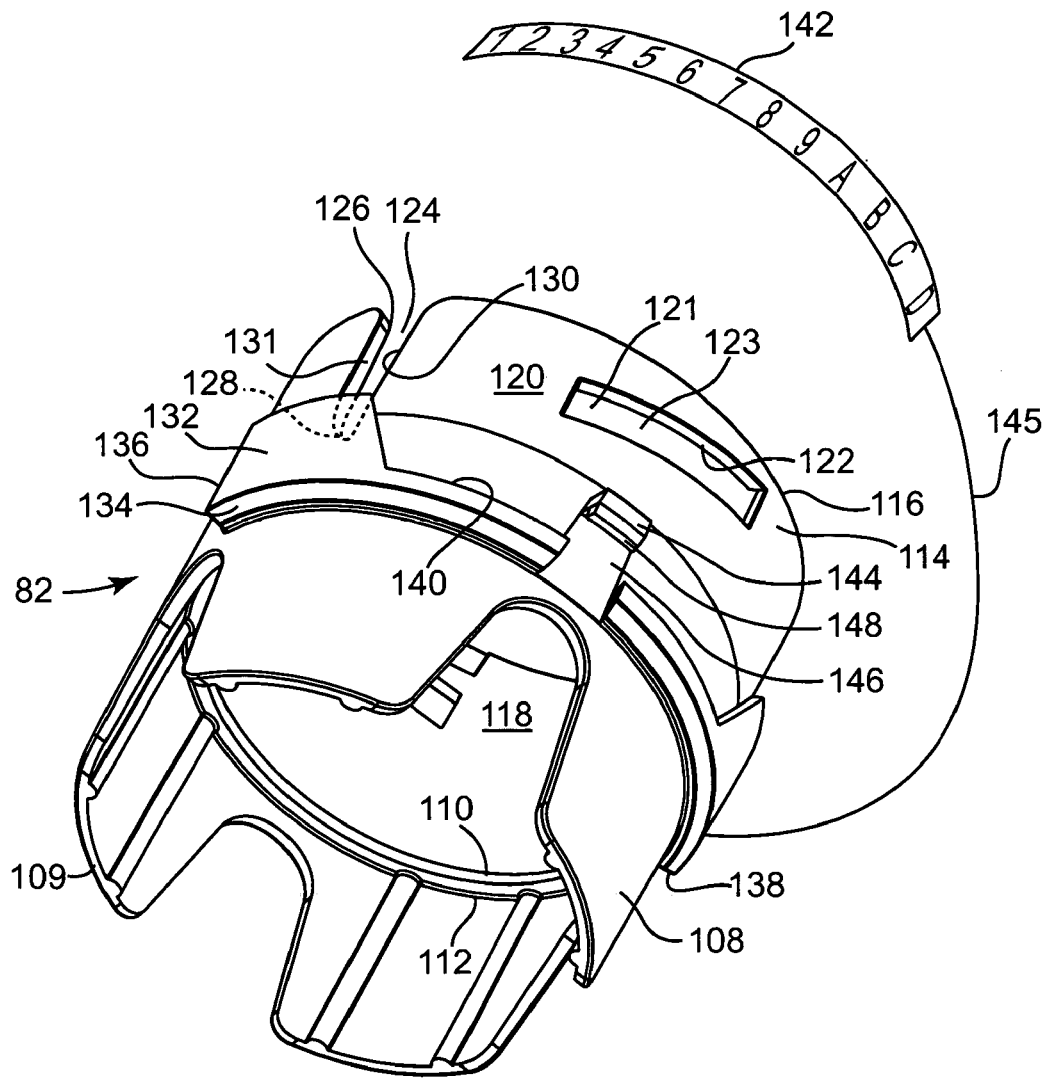
FIG. 5 is a perspective view of a body component.

Referring to FIG. 5, the body 82 has a base 108, a ledge 110 and an upper wall 114. The ledge is formed between the base 108 and the upper wall 114. The base 108 has a first end 109 on the bottom 68 of the jar 56 and a second end 112 on the ledge 110. The upper wall 114 extends from the ledge 110 opposite the base 108 to a lid end 116. When the retainer is in the jar 56, the base 108 and upper wall 114 form a hollow structure concentric with the storage chamber 30. The base is on the jar bottom 68 and the lid end 116 is adjacent to and may bear against the lid 12. The ledge 110 is between the base 108 and the lid end 116. The upper wall 114 has a valve side 118 and a jar side 120.

The upper wall 114 has a lock guide 121 formed therein for engaging the cap 84 and guiding the cap 84 to a locked position. The lock guide 121 has a cam surface 122 formed at an angle to the ledge 110 to guide the cap 84 toward the ledge 110 and into a locked position 115 (FIG. 3). The upper wall 114 has a lock adapter 123 formed therein for capturing and removably retaining the cap on the body 82. A locating slot 124 is formed in the upper wall 114. The locating slot 124 opens at the lid end 116 and extends through the upper wall 114 to a position adjacent the ledge 110. The locating slot 124 has an open end 126, a closed end 128 and two spaced edges 130, 131 forming a slot 124 extending from adjacent the ledge 110 and opening at the lid end 116 for engaging the shelf 80.

Preferably, the present invention includes indicia or identification means for the valves. In the embodiment of FIG. 5, the upper wall 114 has a tag pocket 132 on the jar side 120 for retaining a serial number tag 142 on the body 82. The tag pocket 132 has a bottom 134, a first side 136 and second side 138. The tag pocket 132 is open between the first side 136 and the second side 138 to allow the serial number tag 142 to be read from outside the body 82. The tag pocket 132 has open top 140 for insertion and removal of the serial number tag 142. The serial number tag 142 has a tether 145 attached between the tag 142 and the body 82. A tag post 144 is formed on the body 82 adjacent the open top 140 to keep the serial number tag in the pocket 132. The tag post has a spacer 146 and a lip 148. The tag 142 is placed in the tag pocket 132 and is captured between the tag pocket bottom 134 and the tag post lip 148. The serial number tag 142 may have a numeric identification embossed thereon, a barcode, or other identifying marks. The serial number tag 142 may alternatively be a RF Id or other passive or active electronic marker used to identify objects. Also alternatively, the identification means or indicia may comprise a bar code, that is preferably not physically attached to the valve. Other embodiments may include attaching a tag to hooks or pegs on the retainer. In another embodiment, the identification means may comprise engraving, etching, embossing or printing indicia such as a serial number or bar code directly on the retainer or valve holder.

Figure 6:
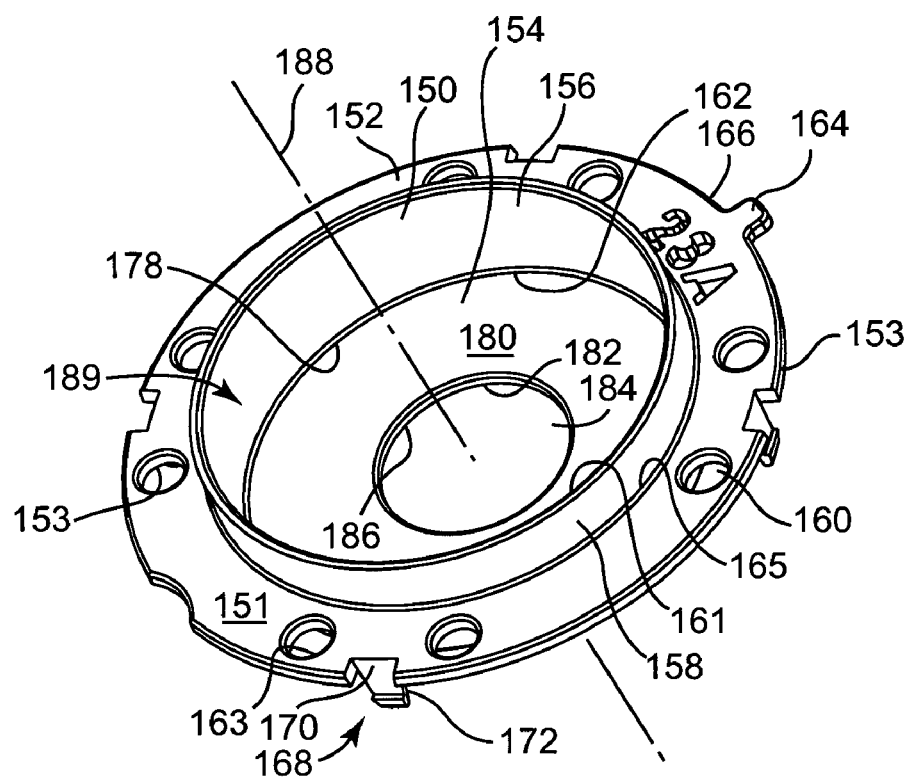
FIG. 6 is a perspective view of a shelf component.

Referring to FIG. 6, a shelf 80 having an aortic valve configuration for supporting an aortic style valve 69 (FIG. 8) is shown. In the aortic configuration, the shelf 80 has a support ring 150, an outer flange 152 and an inner flange 154. The support ring 150 has an inside 156, an outside 158, a top edge 161 and a bottom edge 162. The support ring 150 is cylindrical. The support ring 150 is axially aligned in the storage chamber 30.

The outer flange 152 has inner edge 165 on the outside 158 of the support ring 150, a top 151 and a bottom 153. The outer flange 152 extends outwardly from the support ring 150. The outer flange 152 is disposed between the valve pocket 189 and the jar 56. The outer flange 152 has a plurality of drain holes 160 formed therein by drilling or molding. Each drain hole 160 has a periphery 163 defined by the edge of the drain hole 160. The drain holes 160 extend from the top 151 to the bottom 153 of the outer flange 152.

Continuing to refer to FIG. 6, the inner flange 154 forms a bottom to the valve pocket 189. Inner flange 154 has an outer edge 178 on the inside 156 of the support ring 150 adjacent the bottom edge 162. The inner flange 154 has a top 180, a bottom 182 and a drain hole 184. The drain hole 184 has an edge 186 and an axis 188. The inner flange 154 and the support ring 150 form a valve pocket 189 on the shelf 80. The valve 69 is positioned in the valve pocket 189 to protect from damage. The configuration of FIG. 6 illustrates the valve pocket 189 with the inner flange 154 acting as the bottom surface. The valve pocket 189 is circumferentially surrounded by the support ring 150.

A locating tab 164 extends from the outer edge 166 of the outer flange 152. The locating tab 164 is sized to slidably fit in the locating slot 124 in the upper wall 114 of the body 82. A plurality of snap fingers 168 are formed along the outer edge 166. The snap fingers 168 have a standoff 170 and a latch 172. The latch 172 is spaced from the bottom 153 of the outer flange 152. The snap fingers 168 are made of a resilient material such as PVC or other plastic compounds and may be molded as part of the shelf.

Figure 6A:
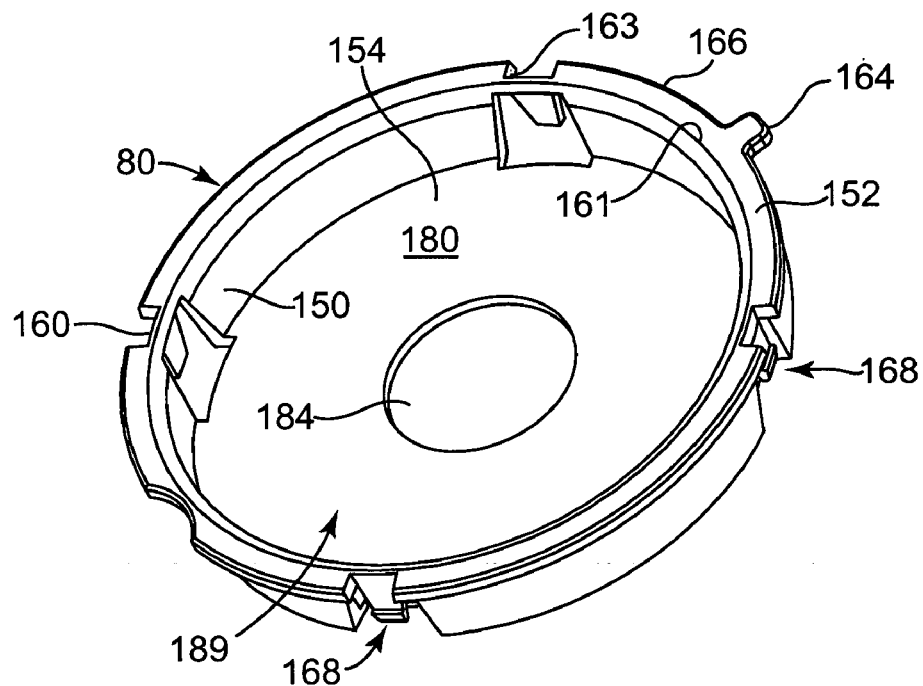
FIG. 6a is a perspective view of an alternative embodiment of a shelf component.

A larger size aortic valve configuration shelf 80 is shown in FIG. 6a. The shelf 80 has an outer flange 152 located at the top edge 161 of the support ring 150. The valve pocket 189 is enlarged by a larger diameter support ring 150 and a more narrow outer flange 152. The drain holes 160 are formed adjacent to and with the snap fingers 168. In this embodiment, the drain hole periphery 163 is part of the outer edge 166. The snap fingers 168 append from the drain hole periphery 163. A drain channel is formed in the snap finger 168 to help drain liquid past the shelf 84. The outer flange 152 spaces the valve pocket 189 from the sidewall 64 and engages the body 82 by attaching to the ledge 110. The support ring 150 surrounds the valve pocket 189. The outer edge 166 bears against the body 82 (FIG. 5) to space the support ring 150 away from the retainer.

Figure 6B:
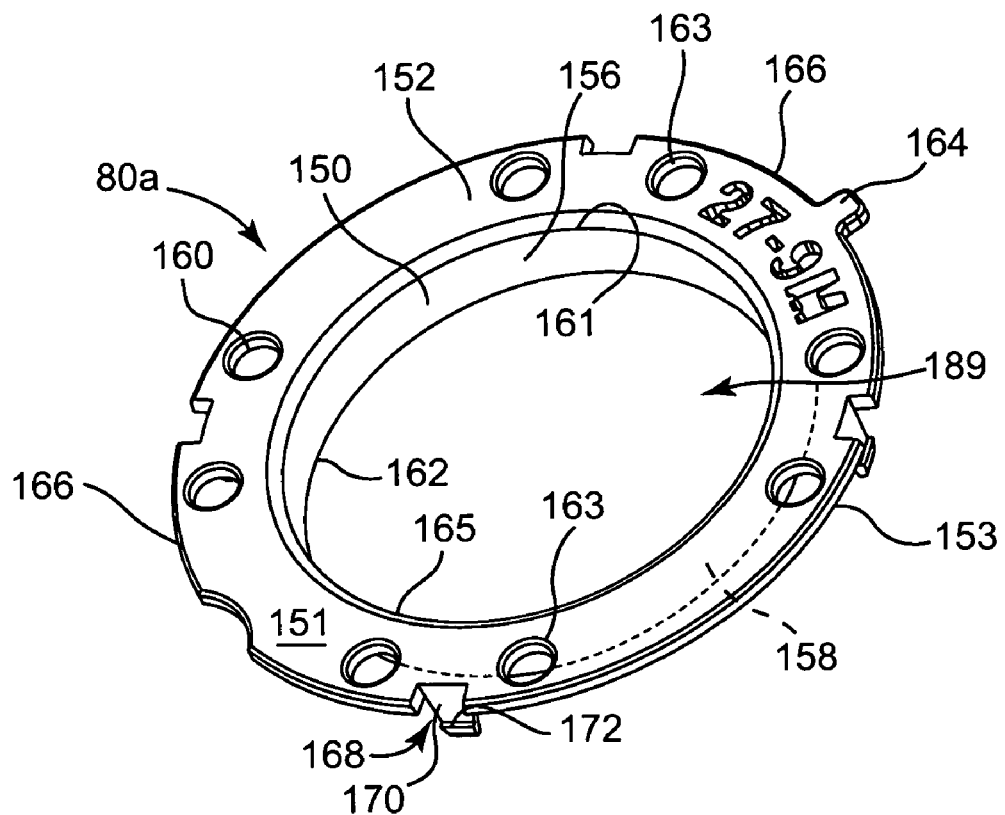
FIG. 6b is a perspective view of an alternative embodiment of a shelf component.

An alternate preferred embodiment is shown in FIG. 6b comprising a shelf 80a having a mitral valve configuration. The mitral valve configuration for supporting a mitral style valve 69a has an open bottom on valve pocket 189. The mitral valve configuration shelf 80a comprises a support ring 150 and an outer flange 152. The support ring 150 has an inside 156, an outside 158, a top edge 161 and a bottom edge 162. The outer flange further comprises an outer edge 166, a top 151 and a bottom 153. The outer flange 152 is on the top edge 161 and extends outward to engage the body 82. The support ring 150 extends from the bottom 153 of the outer flange 152. The outer flange 152 has a plurality of drain holes 160 extending through the flange from the top 151 to the bottom 153. Each drain hole 160 has a periphery 163 defined by the edge of the drain hole 160. The drain holes 160 extend through the shelf 80 at the outer flange 152. The drain holes 160 may be round or other shapes to allow liquid to flow past the shelf 80.

The inside 156 of the support ring 150 defines the valve pocket 189 for containing the portion of the valve 69a hanging below the outer flange 152. The mitral valve 69a (FIG. 9) sits in the valve pocket 189 having the sewing ring 74 on the outer flange 152 and the leaflets extending or dangling between the sewing ring 74 and the bottom of the container, or away from the valve holder 75.

Figure 6C:
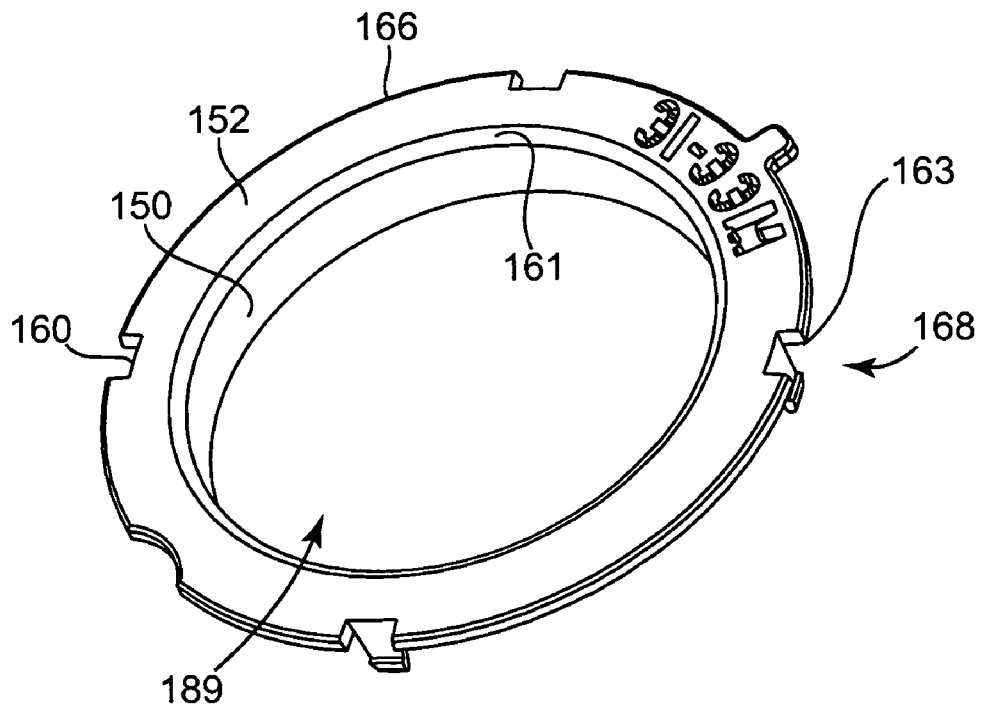
FIG. 6c is a perspective view of an alternative embodiment of the shelf component.

A larger size version of the mitral configuration shelf 80a of FIG. 6b is shown in FIG. 6c having the outer flange 152 located at the top edge 161 of the support ring 150. The larger valve size requires a larger diameter support ring 150. The drain holes 160 are formed in the outer flange 152 along the outer edge 166. The snap fingers 168 are formed in the periphery of the drain holes 160. In this embodiment, the drain hole periphery 163 is part of the outer edge 166 defined by an indent or notch. The snap fingers 168 append from the drain hole periphery 1653.

Figure 7:
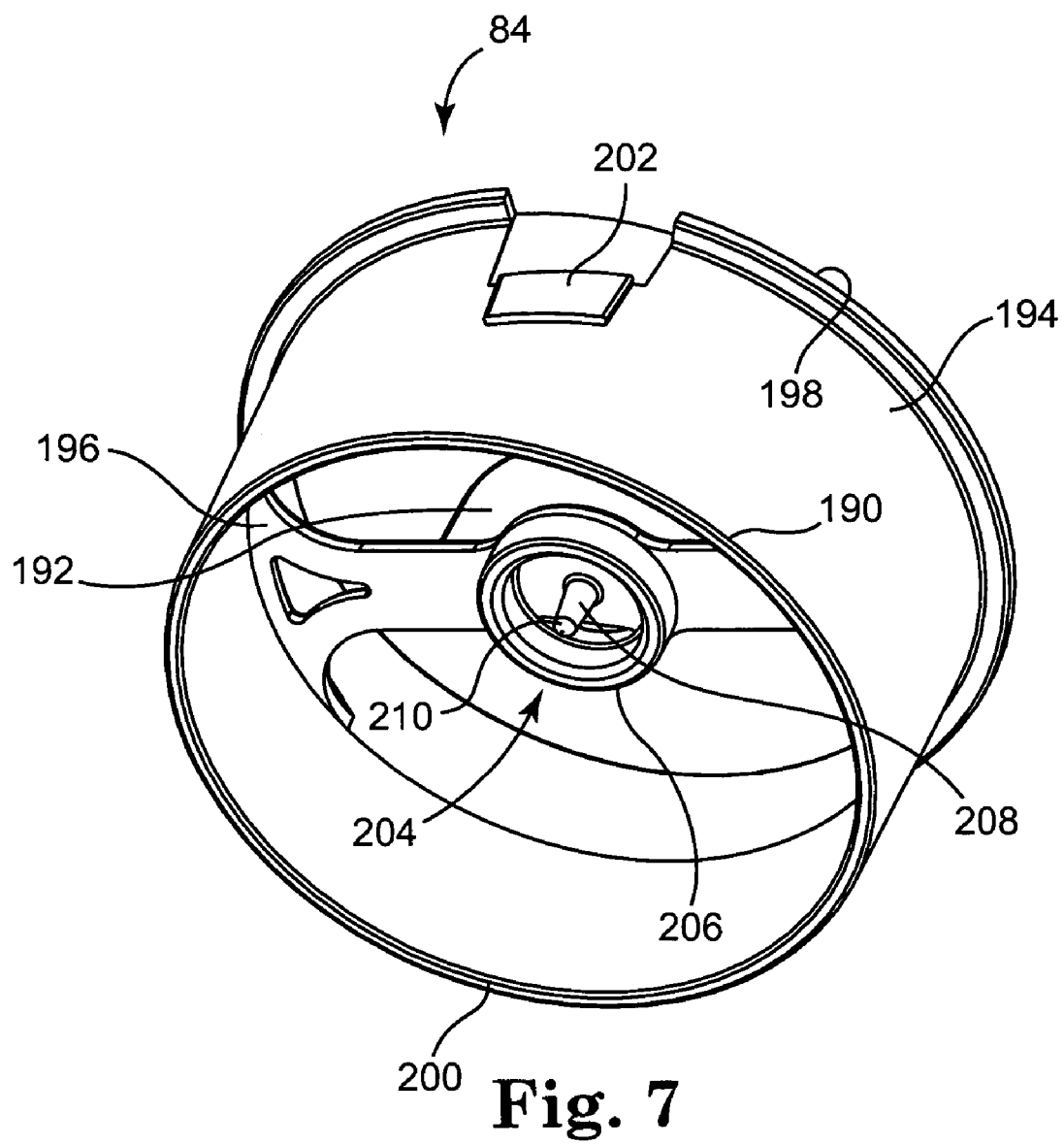
FIG. 7 is a perspective view of a bottom portion of a cap.

Referring to FIG. 7, the cap 84 has a shell 190 and a handle 192. The cap 84 is configured to removably attach to the upper wall 114 (FIG. 5) by a quarter turn lock. The shell 190 has a generally cylindrical shaped wall 194 having a top 198 and a bottom 200. A lock 202 is formed on the wall 194. The lock 202 is sized and positioned to slidably engage the body 82 (FIG. 5) as is well known in the art of quarter turn fasteners. The cap 84 may be attached to the lid 12. The handle 192 is radially attached to the shell 190 having a valve positioner 204 thereon.

The valve positioner 204 is attached to and spaced from the shell 190. The handle 192 has a first end 196 attached to the inside of the shell 190. The valve positioner 204 comprises a retaining ring 206 and a locating peg 208. The locating peg 208 has end 210 on the peg 208. The valve positioner 204 appends from the handle 192 to encircle and capture the handle adapter 76 (FIG. 3) with the retaining ring 206 and the locating peg 208.

Figure 8:
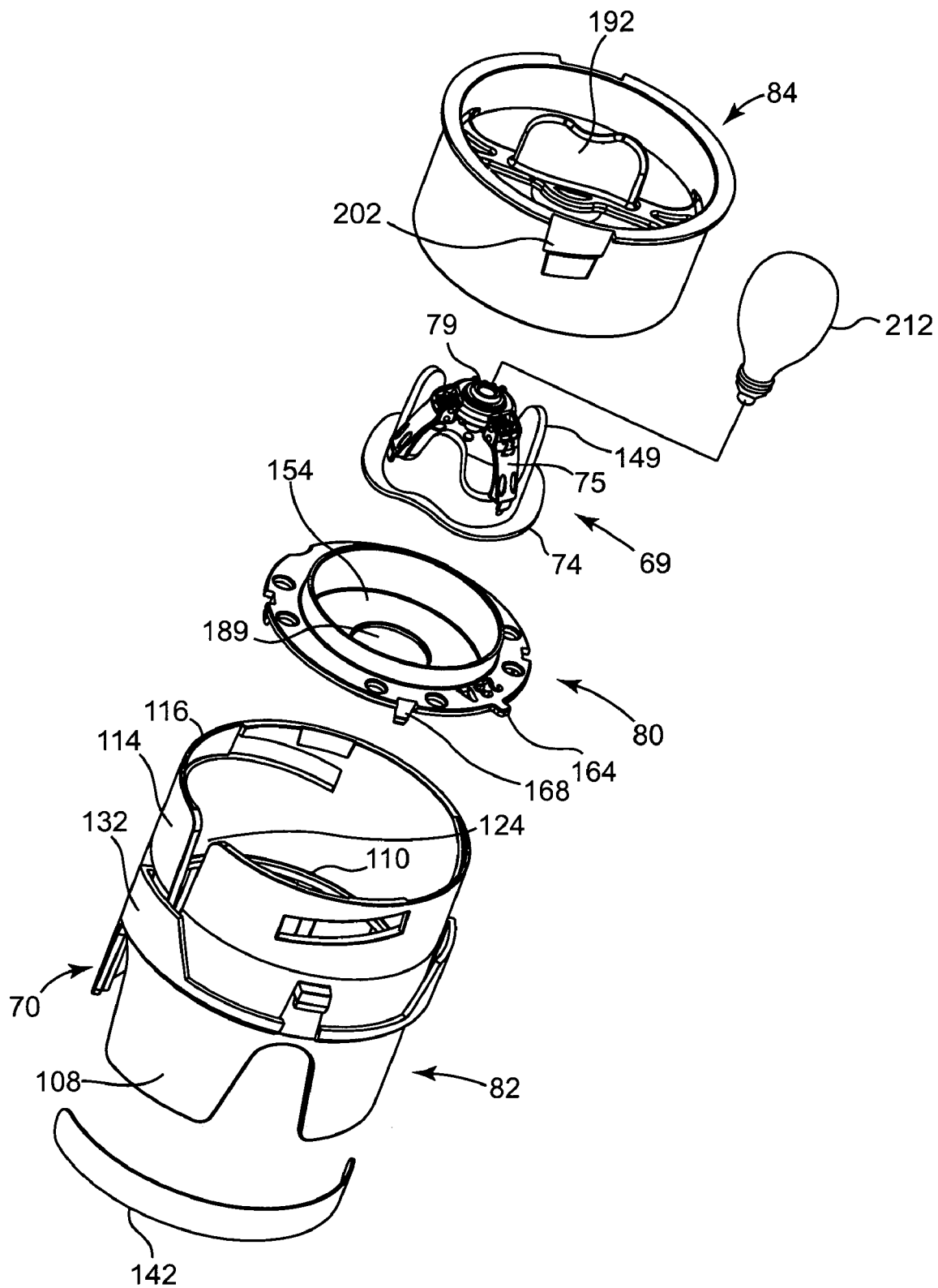
FIG. 8 is an exploded perspective view of the valve retainer with an aortic valve mounted in a holder several components.

Referring to FIG. 8, a retainer 70 for an aortic valve 69 is shown in exploded perspective. The retainer has a body 82 with a ledge 110 between the base 108 and upper wall 114. The shelf 80 is selected for the valve 69 size and configuration to be packaged. The aortic configuration shelf 80 has an outer flange 152, a support ring 150 and an inner flange 154. The valve 69 is attached to a sewing ring 74 on a valve holder 75. The valve holder 75 has a handle adapter 79. The handle adapter 79 has threaded hole 81 for threadably attaching a valve handle 212 to the valve holder 75. The valve handle 212 may be attached by threads, a snap fit or other releasable fastening method. The cap 84 has a lock 202 and a valve positioner 204.

The shelf is attached to the ledge 110 by the snap fingers 168 and the locating tab 164. The sewing ring 74 is on the inner flange 154. The valve 69 is surrounded by the support ring 150. The handle adapter 79 is oriented toward the lid end 116 to engage the cap 84 and facilitate insertion of the handle 212 for removing the valve 69 from the retainer. The leaflets 149 of the valve 69 are shown in aortic configuration positioned above the sewing ring 74. The cap 84 is concentrically inserted into the body at the second lid end 116. The cap engages the valve 69 at valve holder 75 with the valve positioner 204 (FIG. 3). The valve is held between the shelf 80 and the cap 84. The retainer 70 having the valve 69 inside is placed in the jar 56.

The handle 192 is used to move the retainer 70 in and out of the jar 56. The sterilizing solution 73 drains through the drain holes 160, 184. After removal from the jar 56, the retainer 70 may be used to hold the valve 69 outside of the jar prior to rinsing. The handle 192 is turned a quarter turn to unlock the cap 84 from the body 82. The cap 84 is removed from the body 82. The valve handle 212 is screwed into the handle adapter 79. The valve 69 is removed from the system to be prepared for use.

Figure 9:
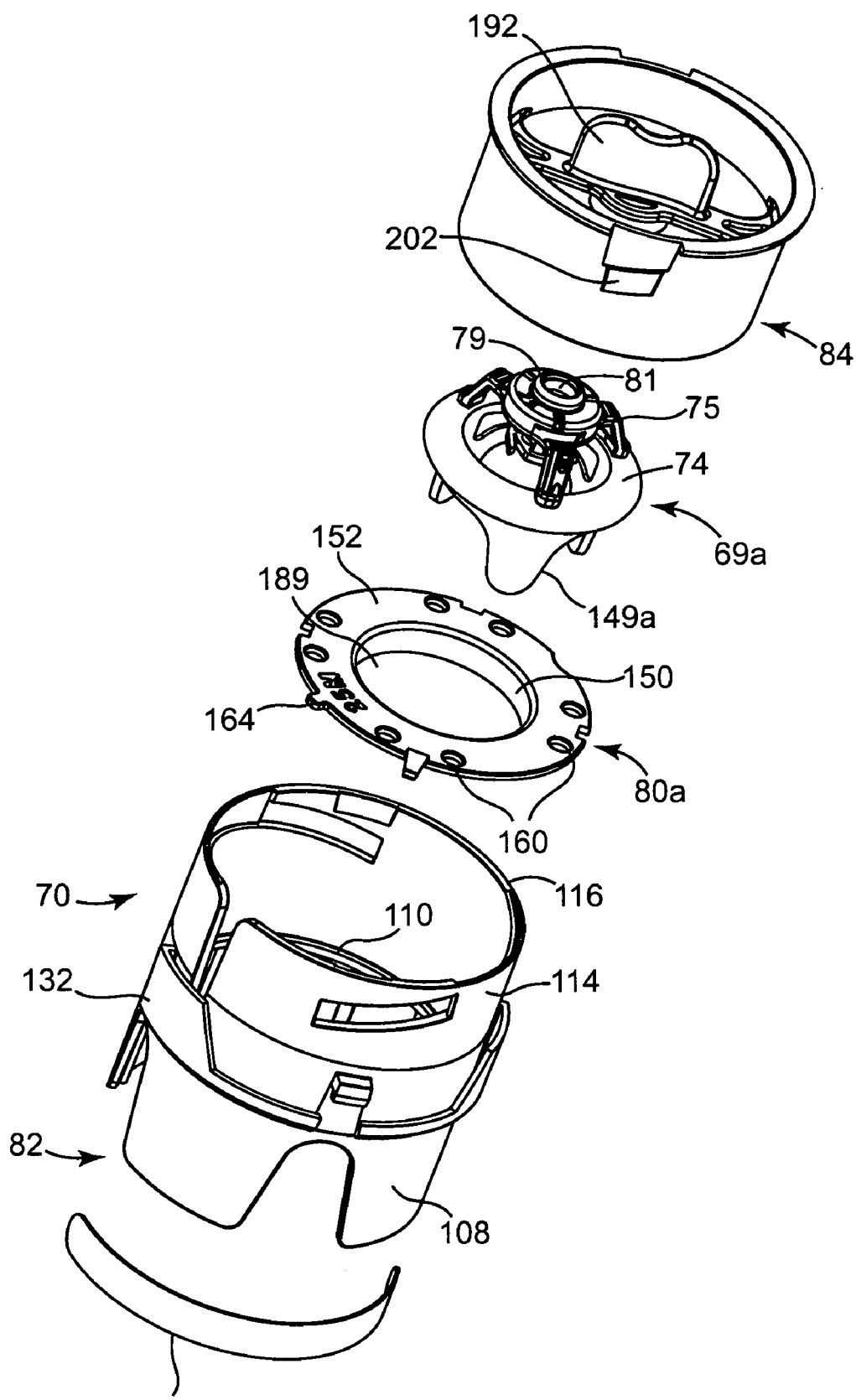
FIG. 9 is an exploded perspective view of the valve retainer with an aortica mitral valve mounted in a holder.

Referring to FIG. 9, a retainer 70 and a valve 69a having a mitral configuration is shown in exploded perspective. The retainer 70 has a body 828 with a ledge 110 between the base 108 and the upper wall 114. The shelf 80a is selected for the mitral valve 69a size and configuration to be packaged. The mitral configuration shelf 80a has an outer flange 152 and a support ring 150. The mitral valve 69a is attached to a sewing ring 74 on a valve holder 75. The valve holder 75 has a handle adapter 79. The handle adapter 79 has threaded hole 81 for threadably attaching a valve handle 212 to the valve holder 75. The valve handle 212 may be attached by threads, a snap fit or other releasable fastening method. The cap 84 has a lock 202 and a valve positioner 204.

The shelf 80a is attached to the ledge 110 by the snap fingers 168 and the locating tab 164. The sewing ring 74 is on the outer flange 152. The leaflets 149a of the valve 69a are shown in mitral configuration positioned below the sewing ring 74, away from the valve holder 75. The valve 69a is surrounded by the support ring 150 having the leaflets 149a extending toward the base 108. The handle adapter 79 is oriented toward the lid end 116 to engage the cap 84 and facilitate insertion of the handle 212 for removing the valve 69a from the retainer 70. The cap 84 is concentrically inserted into the body 82 at the lid end 116. The cap 84 engages the valve holder 75 with the valve positioner 204. The mitral valve 69a is held between the shelf 80 and the cap 84. The retainer 70 having the valve 69a inside is placed in the jar 56.

In use, the valve 69 is manufactured having a sewing ring 74 circumferentially attached. A valve holder 75 is removably attached to the sewing ring 74. The valve 69 is sterilized. The appropriate shelf 80 is selected and sterilized with the body 82, cap 84, jar 56 and lid 12. The shelf 80 is inserted into the body 82 having the locating tab 164 in the slot 124 and the snap fingers 168 on the ledge 110. The valve 69 is placed in the valve pocket 189 resting on the sewing ring 74 and oriented with the handle adapter 796 toward the lid end 116 of the body 82. The cap 84 is concentrically inserted into the body 82 having the valve 69 between the shelf 80 and the cap 84. The handle adapter 79 is adjusted to engage the valve positioner 204 and the cap is turned to lock the cap 84 into the body 82.

The retainer 70 having the valve 69 contained therein is placed in the jar 56 and the lid 12 is attached. The sterilized solution is dispensed into the jar through one or more fill holes 28, 44 to prevent spilling or splashing on a sealing surface of the lid 12 or the jar 56. The respective tab 32, 46 adjacent each fill hole is bent over to cover the fill hole and is ultrasonically welded to the lid 12 to seal the fill hole. The tamper evident seal 50 is attached over the jar 56 and the lid 12.

The apparatus 10 with the valve 69 therein is shipped to a facility for use in a patient. The jar 56 is removed from the box and the outside of the jar 56 may be sterilized. The surgery worker grasps the jar 156 and applies an opening force (A) to a flat on the grip surface 18. The tamper evident seal tears at the perforations 60 and the lid 12 is unscrewed from the jar 56. The retainer 70 is removed from the jar allowing the sterilizing fluid 73 to drain through the drain holes 160, 184. The valve 69 may be rinsed while held in the retainer 70.

The worker grasps the body 82 and the cap handle 192 and turns the cap handle 192 with respect to the body 82. The cap 84 releases from the body 82 and is removed. A valve handle 212 is attached to the handle adapter 79. The valve 69 is removed from the retainer 70 attached to the handle 212 and further rinsed and prepared for use.

It will be appreciated that the present invention is suitable for use with a variety of different types of valves such as aortic, tricuspid, pulmonic or mitral valves. The valve is preferably oriented in the jar retainer so that the handle can be conveniently attached directly to the valve holder, without having to re-orient the valve. This minimizes the chance for valve contamination during preparation for surgical implantation.

Although the invention has been described above in connection with particular embodiments and examples, it will be appreciated by those skilled in the art that the invention is not necessarily so limited, and that numerous other embodiments, examples, uses, modifications and departures from the embodiments, are intended to be encompassed by the claims attached hereto. The entire disclosure of each patent and publication cited herein is incorporated by reference, as if each such patent or publication were individually incorporated by reference herein.

What is claimed is:

1. An apparatus for retaining a prosthetic heart valve in a container, the apparatus comprising:

a prosthetic heart valve having a sewing ring wherein a valve holder is attached to the sewing ring, the container having a sidewall, a bottom, an open top, and a lid removably associated with the open top and at least partially defining a closed storage chamber in the container;

a retainer in the container, the retainer having a body and a removable cap comprising a valve positioner engaging the valve holder;

a shelf attached to the body, the shelf comprising a drain hole and a valve pocket wherein the sewing ring is positioned on the shelf and the valve is positioned in the valve pocket, wherein the valve is retained in the valve pocket and held in spaced relation from the container sidewall and bottom;

wherein the shelf further comprises an outer flange and a support ring, the support ring around the valve pocket, the outer flange on the support ring between the valve pocket and sidewall;

wherein the shelf further comprises an inner flange, the support ring having an inside and an outside, the outer flange on the outside, the inner flange on the inside, a drain hole in one or both of the inner flange and the outer flange; and wherein the sewing ring is supported on the inner flange with the support ring circumferentially surrounding the valve.

2. The invention of claim 1 further comprising a tamper evident seal on the container, the tamper evident seal attached to the lid and extending to the container, a perforation in the tamper evident seal disposed between the lid and the container.

3. The invention of claim 1 wherein the valve positioner holds the valve on the shelf.

4. An apparatus for retaining a prosthetic heart valve, the apparatus comprising:

a container having a side wall, an open top, and a closed bottom;

a lid removably associated with the open top to seal the container, the lid comprising a top side, a grip surface, and a sealable fill hole, the grip surface comprising a torque enhancing shape and a bottom edge, the fill hole extending through the lid; and a valve retainer in the container, the valve retainer comprising a first end, a second end, a valve positioner, and a shelf, the first end adjacent the bottom of the container, the second end adjacent the lid, the valve positioner positioned at the second end, the shelf positioned between the first end and the second end, the shelf further comprising an outer flange and a support ring, the outer flange positioned between the sidewall and the support frame ring the support ring on the outer flange, wherein the support ring and the outer flange define a valve pocket whereby a valve can be held in the retainer between the shelf and the valve positioner.

5. The invention of claim 4 further comprising a drain hole in the outer flange.

6. The invention of claim 4 wherein the shelf further comprises an inner flange extending inward from the support ring forming a valve pocket bottom, a drain aperture in the inner flange.

7. The invention of claim 4 wherein the retainer further comprises a body having a generally cylindrical shape.

8. The invention of claim 7 wherein the valve retainer body further comprises an identification means.

9. The invention of claim 7 wherein the retainer further comprises a cap, an identification pocket and a tamper evident seal, the cap on the body, the valve positioner on the cap, the identification tag pocket on the body adjacent the sidewall.

10. The invention of claim 4 wherein the shelf has a mitral valve configuration for supporting a mitral valve in the valve pocket.

11. The invention of claim 4 wherein the shelf has an aortic valve configuration for supporting an aortic valve in the valve pocket.

12. The invention of claim 4 wherein the torque enhancing shape further comprises a first flat on the grip surface.

13. The invention of claim 4 wherein the lid further comprises a tab on the top side, the tab attached adjacent the fill hole wherein the tab can be folded to a position covering the fill hole and attached to the lid to seal the fill hole.

14. The invention of claim 4 further comprising a tamper evident seal, the tamper evident seal comprising a strip of material having a container end on the container, a flag portion, a lid end on the lid, and a perforation in the seal between the flag portion and the jar end, the perforation disposed adjacent the bottom of the lid.

15. A system for retaining a prosthetic heart valve in a container, the system comprising:

a prosthetic valve having a sewing ring attached thereto, a removable valve holder attached to the sewing ring:

a container having a top, a bottom, a circumferential sidewall, and a removable lid defining a storage chamber in the container;

a body in the container, the body having a base on the bottom of the container and an upper wall; and a shelf having an inner flange and outer flange, the outer flange comprising a drain hole therein, a valve pocket, and a support ring around the valve pocket, the support ring having an inside and an outside, the inner flange on the inside and the outer flange on the outside, the outer flange on the support ring between the valve pocket and sidewall, the sewing ring on the shelf, whereby the valve is suspended in the storage chamber in spaced relation to the top, bottom and sidewall of the container.

16. The system of claim 15 further comprising a valve positioner removably attached to the body, the valve positioner engaging the valve holder to retain the valve between the shelf and the valve positioner.

17. The system of claim 16 further comprising a cap attached to the body, the valve positioner on the cap, the valve mounted between the cap and the shelf, the valve positioner disposed to bear against the holder to retain the sewing ring on the shelf.

18. The system of claim 15 wherein the system further comprises a plurality of drain holes formed in the shelf.

19. The system of claim 15 further comprising a tamper evident seal on the container.

20. The system of claim 15 comprising the support ring concentrically mounted in the container and the valve surrounded by the support ring.

21. The system of claim 15 wherein the shelf further comprises a mitral valve configuration.

22. The system of claim 15 wherein the shelf further comprises an aortic valve configuration.

23. An apparatus for retaining a prosthetic heart valve in a container, the apparatus comprising:

a prosthetic heart valve having a sewing ring wherein a valve holder is attached to the sewing ring, the container having a sidewall, a bottom, an open top, and a lid removably associated with the open top and at least partially defining a closed storage chamber in the container;

a retainer in the container, the retainer having a body; and a shelf attached to the body, the shelf comprising a valve pocket, a support ring around the valve pocket, an inner flange on the inside of the support ring, an outer flange on the outside of the support ring and between the valve pocket and sidewall, and a drain hole formed in the outer flange wherein the sewing ring is positioned on the shelf and the valve is positioned in the valve pocket, wherein the valve is retained in the valve pocket and held in spaced relation from the container sidewall and bottom.

24. The invention of claim 23 wherein the shelf further comprises a drain hole in the inner flange wherein the sewing ring is supported on the inner flange with the support ring circumferentially surrounding the valve.

25. An apparatus for retaining a prosthetic heart valve, the apparatus comprising:

a container having a side wall, an open top, and a closed bottom;

a lid removably associated with the open top to seal the container, the lid comprising a top side, a grip surface, and a sealable fill hole, the grip surface comprising a torque enhancing shape and a bottom edge, the fill hole extending through the lid; and a valve retainer in the container, the lid comprising a tab on the top side, the tab attached adjacent the fill hole wherein the tab can be folded to a position covering the fill hole and attached to the lid to seal the fill hole, the valve retainer comprising a first end, a second end, a valve positioner, and a shelf, the first end adjacent the bottom of the container, the second end adjacent the lid, the valve positioner positioned at the second end, the shelf positioned between the first end and the second end, whereby the valve is held in the retainer between the shelf and the valve positioner.

26. An apparatus for retaining a prosthetic heart valve, the apparatus comprising:

a container having a side wall, an open top, and a closed bottom;

a lid removably associated with the open top to seal the container, the lid comprising a top side, a grip surface, and a sealable fill hole, the grip surface comprising a torque enhancing shape and a bottom edge, the fill hole extending through the lid; and a valve retainer in the container, the valve retainer comprising a generally cylindrical body having a first end, a second end, a valve positioner, and a shelf, the first end adjacent the bottom of the container, the second end adjacent the lid, the valve positioner positioned at the second end, the shelf positioned between the first end and the second end, the retainer further comprises a cap, an identification pocket and a tamper evident seal, the cap on the body, the valve positioner on the cap, the identification tag pocket on the body adjacent the sidewall, whereby the valve is held in the retainer between the shelf and the valve positioner.

* * * * *